(12) United States Patent
Sopori

(10) Patent No.: US 6,275,295 B1
(45) Date of Patent: Aug. 14, 2001

(54) OPTICAL SYSTEM FOR DETERMINING PHYSICAL CHARACTERISTICS OF A SOLAR CELL

(75) Inventor: Bhushan L. Sopori, Denver, CO (US)

(73) Assignee: Midwest Research Institute, Kansas City, MO (US)

(*) Notice: Subject to any disclaimer, the term of this patent is extended or adjusted under 35 U.S.C. 154(b) by 0 days.

(21) Appl. No.: 09/302,727

(22) Filed: Apr. 30, 1999

(51) Int. Cl.⁷ .................................................. G01N 21/47
(52) U.S. Cl. ............................................. 356/446; 356/236
(58) Field of Search .................................. 356/236, 446; 250/228

(56) References Cited

U.S. PATENT DOCUMENTS

| | | |
|---|---|---|
| 4,511,800 | 4/1985 | Harbeke et al. . |
| 4,583,861 | 4/1986 | Yamaji et al. . |
| 4,923,779 | 5/1990 | Keane . |
| 4,972,092 * | 11/1990 | Schmitt et al. ............... 356/236 |
| 5,268,749 | 12/1993 | Weber et al. . |
| 5,334,844 | 8/1994 | Pollard et al. . |
| 5,367,174 | 11/1994 | Bazile et al. . |
| 5,406,367 | 4/1995 | Sopori . |
| 5,537,203 | 7/1996 | Carr . |
| 5,796,484 | 8/1998 | Honma et al. . |

OTHER PUBLICATIONS

Sopori, B.L., Principle of a New Reflectometer for Measuring Dielectric Film Thickness on Substrates of Arbitrary Surface Characteristics, Rev., Sci. Instrum., vol. 59, No. 5 (May, 1988), pp. 725–727.

* cited by examiner

*Primary Examiner*—Richard A. Rosenberger
(74) *Attorney, Agent, or Firm*—Paul J. White

(57) ABSTRACT

The invention provides an improved optical system for determining the physical characteristics of a solar cell. The system comprises a lamp means for projecting light in a wide solid-angle onto the surface of the cell; a chamber for receiving the light through an entrance port, the chamber having an interior light absorbing spherical surface, an exit port for receiving a beam of light reflected substantially normal to the cell, a cell support, and an lower aperture for releasing light into a light absorbing baffle; a means for dispersing the reflection into monochromatic components; a means for detecting an intensity of the components; and a means for reporting the determination.

22 Claims, 8 Drawing Sheets

OPTICAL SYSTEM FOR DETERMINING PHYSICAL CHARACTERISTICS OF A SOLAR CELL

CONTRACTUAL ORIGIN OF THE INVENTION

The United States Government has rights in this invention pursuant to Contract No. DE-AC36-98G0-10337 between the United States Department of Energy and the Midwest Research Institute.

BACKGROUND OF THE INVENTION

1. Field of the Invention

This invention relates to an optical system for monitoring the optical quality of solar cells, and more particularly to a reflectance measuring system for use in monitoring the surface texture, metallization, and anti-reflective coating of solar cells in commercial production.

2. Description of the Prior Art

In the fabrication of photovoltaic cells it is necessary to precisely control the sawing, cleaning, texturing, dielectric-film-coating, and metallization process steps. Texture-etching is used to improve the light trapping ability of a solar cell, by reducing the surface reflectance over a broad light spectrum. Texture-etching is also used to remove any saw damage to the surface of a cell. Deposition of a dielectric-film layer, over the textured surface, is used to further reduce reflectance. Metallization of the cell includes alloying an aluminum back contact, and screen printing a front metal contact to the cell. Any failure to tightly control these process steps lends itself to the fabrication of devices, which exhibit a variance in the light-trapping ability, photo-current, fill-factor, and the open-circuit voltage of the cell. Accordingly, there is a need for an optical system useful in the quality control of these process steps.

Various optical systems are available for monitoring the physical characteristics of a photocell. In the prior art, many of these systems measure sample reflectance in a light integrating sphere. The light reflected from the sample is measured spectroscopically. For example, as described in U.S. Pat. Nos. 4,932,779, and 5,406,367, for color measurement, an integrating sphere is provided to receive light, from a light source, through an entrance port. The diffusely reflecting interior walls, of the sphere, reflect the light in multiple reflections, such that a uniform diffuse illumination is provided over the interior surface of the integrating sphere. The integrating sphere is provided with a port designed to receive a sample, the color of which is to be measured. When a sample is positioned over the sample port, the surface of the sample is illuminated with uniform diffuse illumination, reflected from the walls of the integrating sphere. An exit port is located on the sphere, opposite the sample port, for receiving diffusely reflected light from the sample, and the light passing through the exit port is separated into monochromatic components. The intensities of the components are measured, to determine the reflectance of the sample, for each monochromatic component. However, as demonstrated in the foregoing patents, an integrating sphere is used to analyze a small sample area, because the sample, itself, disrupts integration of the illumination. Because commercially sized samples have a large, 4 by 4 inch, surface, it would be necessary to provide an unreasonably large integrating sphere, to rapidly monitor the surface area of a solar cell.

In Sopori, B. L., *Principle of a New Reflectometer for Measuring Dielectric Film Thickness on Substrates of Arbitrary Surface Characteristics*, Rev, Sci. Instru. Vol. 59 no. 5 (May, 1988), pp. 725–727, a reciprocal optical principle, and a relative small light-absorbing sphere, has been used to determine the thickness of an antireflection film, layered over a silicon cell. The reciprocal principle is based on the projection of incident light, at a wide solid-angle of direction, at the sample surface and detecting the intensity of a reflection, normal to the sample surface. The reflectometer comprises a metallic, spherical, dome having openings for two ELH-tungsten-halogen lamps and elliptical reflectors. One lamp is located on each side of the dome. An exit aperture and lens assembly is located at the top of the dome for emitting the reflection. At the base of the dome, diametrically opposed to the exit aperture is a highly absorbing sample support. The support is covered with small-grain polycrystalline sheets, etched and layered with a $Si_3N_4$ deposit, in order to reduce reflectance. Located at the top of the dome is a monochromator and detector, connected to a display device. The display generates a reflection intensity distribution curve for the reflection. The reflectance of a textured sample, having an antireflection coating, exhibits a minimum intensity, on the curve, which is useful in determining the thickness of the film, according to the equation: $t=\lambda_0/4_n$, where $\lambda_0$ is the wavelength having a least reflectance, t is the thickness, and n is the refractive index of the film.

The absorbing and light integrating spheres are similar in construction, but the absorbing sphere must function to eliminate all, extraneous, scattered light. In doing so, the normal reflection is the only light detected. The major extraneous light-scattering source, in an absorbing sphere, is the cell support. While etching a fine grain polycrystalline silicon wafer and depositing a layer of $Si_3N_4$ has produced a non-reflecting support, the monitoring system, according to this invention, provides a significantly different light absorbing baffle and a non-reflecting chuck in lieu of the silicon wafer support. Other significant differences are also included. This invention provides for an increase in the spectrum of projected light in order to generate a reflection from the back-side-contact, is able to monitor the area, thickness, and symmetry of a front-contact, and, because some venders produce cells having a specular surface, is able to monitor the characteristics of a cell having a polished or specular finish. These improvements are desirable in a system, which is useful, to monitor the texture, antireflective film, and metallization properties of solar cells in commercial production.

Thus, in view of the foregoing considerations, there is an apparent need for an optical system which is cost efficient, versatile in use, and capable of arriving at a rapid precise determination of the texture, metallization, and dielectric film optical properties of solar cells in commercial production.

SUMMARY

In view of the foregoing, it is a general object of the present invention to provide an improved optical system which is cost efficient, versatile in use, and capable of arriving at a rapid precise determination of the texture, metallization, and dielectric film optical properties of solar cells in commercial production.

Another object of the invention is to provide an optical system for precisely comparing the optical properties of solar cells after sawing, texturing, cleaning, antireflective coating, and metallization fabrication steps with a predetermined value.

Another object of the invention is to provide an improved system to determine dielectric film thickness.

Another object of the invention is to provide an improved system to determine the surface texture of a solar cell.

It is yet another object of the invention to provide a system to determine the area, thickness, and symmetry of a front-metal-contact, and the optical quality of a back-contact to a solar cell.

The foregoing specific objects and advantages of the invention are illustrative of those which can be achieved by the present invention and are not intended to be exhaustive of limiting of the possible advantages which can be realized. Thus, those and other objects and advantages of the invention will be apparent from the description herein or can be learned from practicing the invention, both as embodied herein or as modified in view of any variations which may be apparent to those skilled in the art.

Briefly, the invention provides an improved optical system for determining the physical characteristics of a solar cell. The system comprises a lamp means for projecting light in a wide solid-angle onto the surface of the cell; a chamber for receiving the light through an entrance port, the chamber having an interior light absorbing spherical surface, an exit port for receiving a beam of light reflected substantially normal to the cell, a cell support, and an lower aperture for releasing light into a light absorbing baffle; a means for dispersing the reflection into monochromatic components; a means for detecting an intensity of the components; and a means for reporting the determination.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

DESCRIPTION OF THE PREFERRED EMBODIMENTS

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

Figure 1:
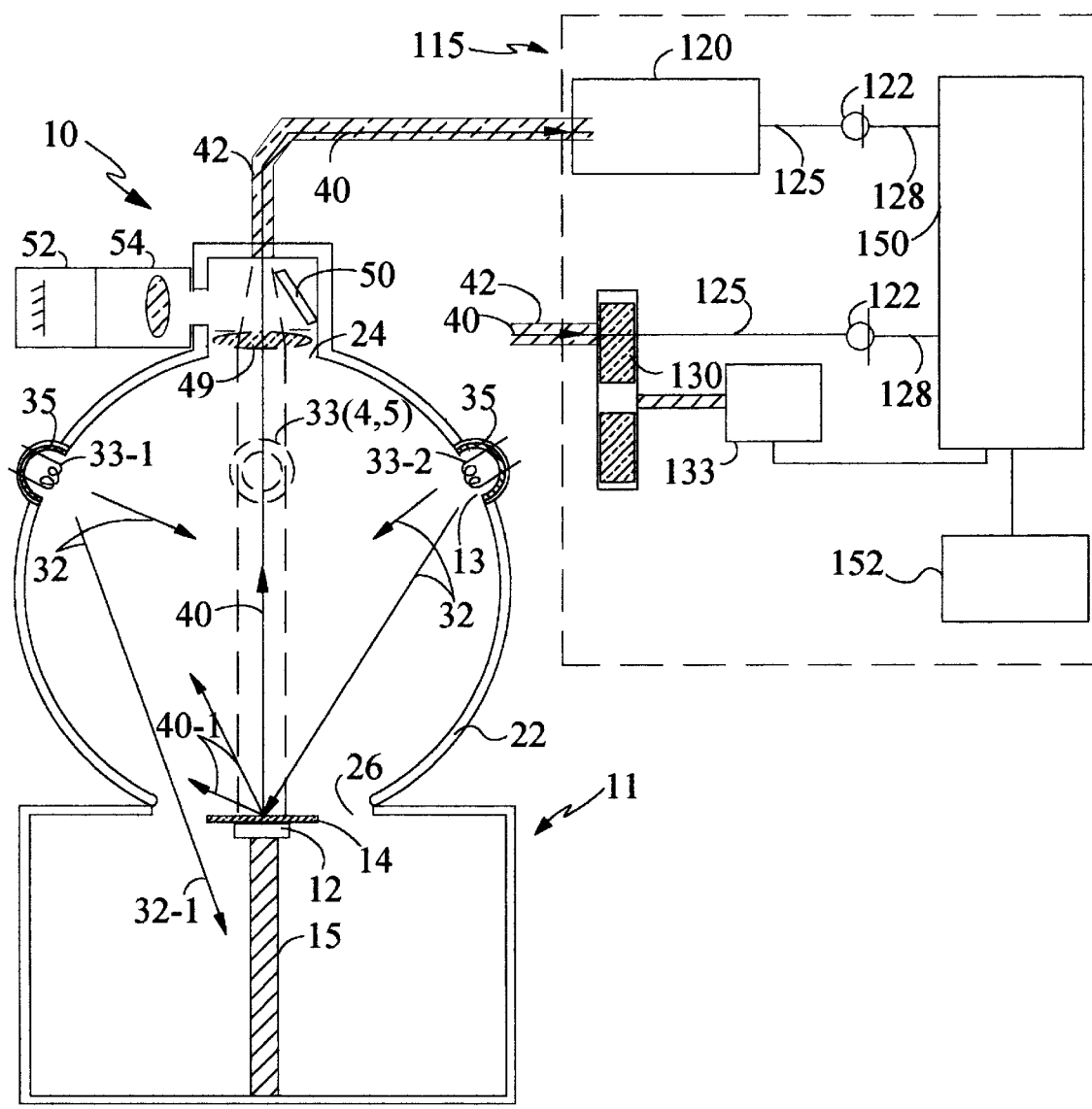
FIG. 1 is a sectional view of one embodiment of the optical system according to the present invention.

Referring now to the drawing figures, in which like numerals refer to like components, there is illustrated in FIG. 1, a preferred embodiment of the invention. Reflectometer 10 includes a spherical chamber 22, which is preferably an 18 inch diameter dome. Chamber 22 includes an exit aperture 24 and a diametrically opposed lower aperture 26, which serves as a sample port. Lamps 33(1–4) project incident light 32 at sample 14 in a wide solid-angle of direction. A solid angle is a measure of the angle subtended at the vertex of a cone. Exit aperture 24 is included for emitting a beam of light 40 which is reflected normal to the sample 14. The interior surfaces of the absorbing chamber 22, baffle 11, and post 15 are roughened, and coated with a non-reflective light absorbing coating, such as flat-black paint. This treatment is used to insure that stray light 40-1, 32-1 (e.g. light not reflecting normal to the sample 14 the surface) is substantially absorbed, without an inadvertent reflection passing through the exit port 24. The lower aperture 26 is 8 inches in diameter and circumferentially disposed about the silicon sample 14. A vacuum chuck 12 is positioned below the lower aperture 26 to secure the sample 14 for analysis. The chuck 12 is smaller in size than the sample 14 to be characterized prevent the scattering of light 32, by the chuck 12. The chuck 12 is supported on a movable post 15, which aids in the positioning of sample 14 within aperture 26 for illumination. The light 32, is projected into the chamber 22 via an entrance port 13, and is generated with lamp sources 33-1,2, such as two ENH tungsten-halogen lamps, one on each side of the chamber 22. The lamps have an elliptical metallic beck reflector 35 formed by lining the inside of an existing dichroic reflector with an aluminum foil such that the projected light 32 is in a 400–1200 nm spectral range. The lower aperture 26 is positioned in diametric alignment with the exit port 24. The light absorbing baffle 11 traps light 32-1 passing, sample 14, through aperture 26 in an outward direction from the chamber.

In the practice of the invention, sample 14 is positioned on the vacuum chuck 12, a vacuum is applied, and post 15 is raised such that the sample 14 is circumferentially disposed within the lower aperture 26, of the chamber 22. The sample 14, is illuminated thereby causing the emission of reflected beam 40, outwardly, through the exit aperture 24. The exit port 24 is associated with a lens assembly 49 for convergence of the reflected beam 40. A fiber-optic-cable 42 transmits light beam 40 for dispersion, detection, determination, and reporting 115.

As seen in FIG. 1, fiber optic cable 42 is connected to a monochromator 120, or a filter wheel 130 and servo motor 133 assembly. The fiber optic cable 42 yields a high signal to noise ratio. A strong signal is necessary to determine the precise optical differences among samples. Monochromator 120 or filter wheel 130, disperses reflection 40 into its monochromatic components 125. The components 125 are detected by photo-detectors 122 which generate a, computer-receptive, signal 128 relative to the intensity of the detected component.

The respective intensity for each monochromic component is stored in the memory of a computer 150. The computer 150 determines the relationship between the intensity of the detected reflection and wavelength for each monochromatic component, a thickness of the dielectric film, and the metallization of the sample cell 14. A computerized report illustrates a reflection intensity distribution curve. The report is useful in making a comparison of the surface texture, film thickness, and metallization properties of a sample with a predetermined result. The result maybe, a standard reflection intensity distribution curve, film thickness, or metallization value, which is stored in the RAM or ROM of the computer 150. Display 152 illustrates the determination, and is used to sequentially monitor the physical quality of solar cells throughout the fabrication process.

Figure 2:
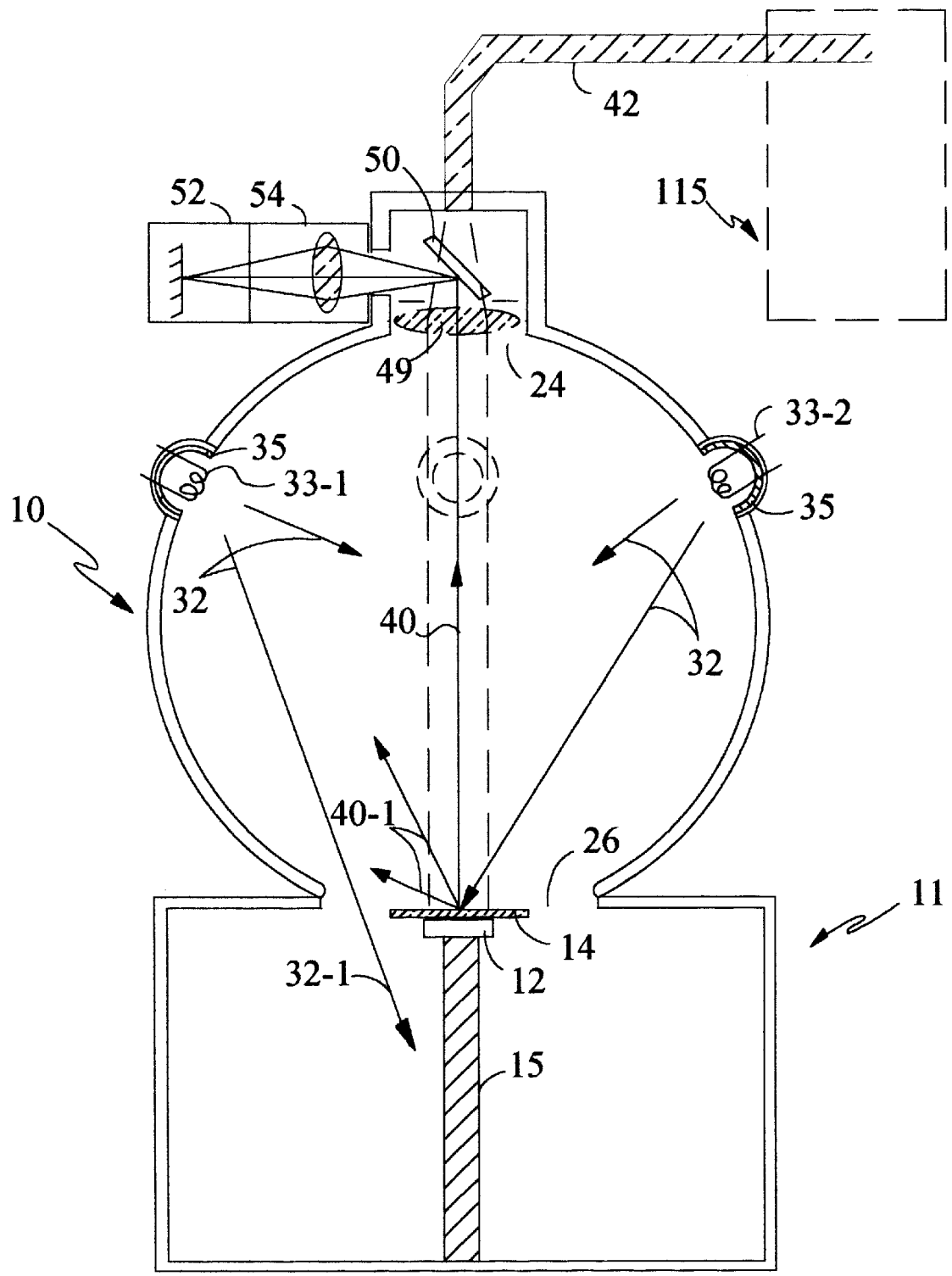
FIG. 2 is a sectional view of the optical system illustrated in FIG. 1 showing the mode of operation for imaging a sample.

Referring now to FIG. 2, it is generally shown therein a sectional view of the optical system illustrated in FIG. 1, as modified to display an image of the sample. To view an image of the cell 14, slidable mirror or prism 50 is located into the path of reflected beam 40. Beam 40 is, thereby, deflected in the direction of a digital camera 52 and its zoom lens 54. Those rays, which fall in the path of the field-of-view of the camera 52, become the object image from, which a real image of sample 14 is created. The real image may be viewed on a control monitor (not shown), associated with the video camera 52. An optical filter (not shown) may be located in the optical path of the camera, to provide a variety of useful information. For example, an image of any variations in the thickness of a film, over the sample surface, is shown when using a filter passing waves at $\lambda_o$, in a system calibrated according to the equation: $(\lambda_o)=4nt$; where $\lambda_o$ is the monochromatic component having the least reflectance; t is the thickness, and n the refractive index of the film. One skilled in the art will also appreciate that camera 52 may also include a provision for a video tape recording, or input into the memory of computer 150, for permanent documentation of the image.

Figure 3:
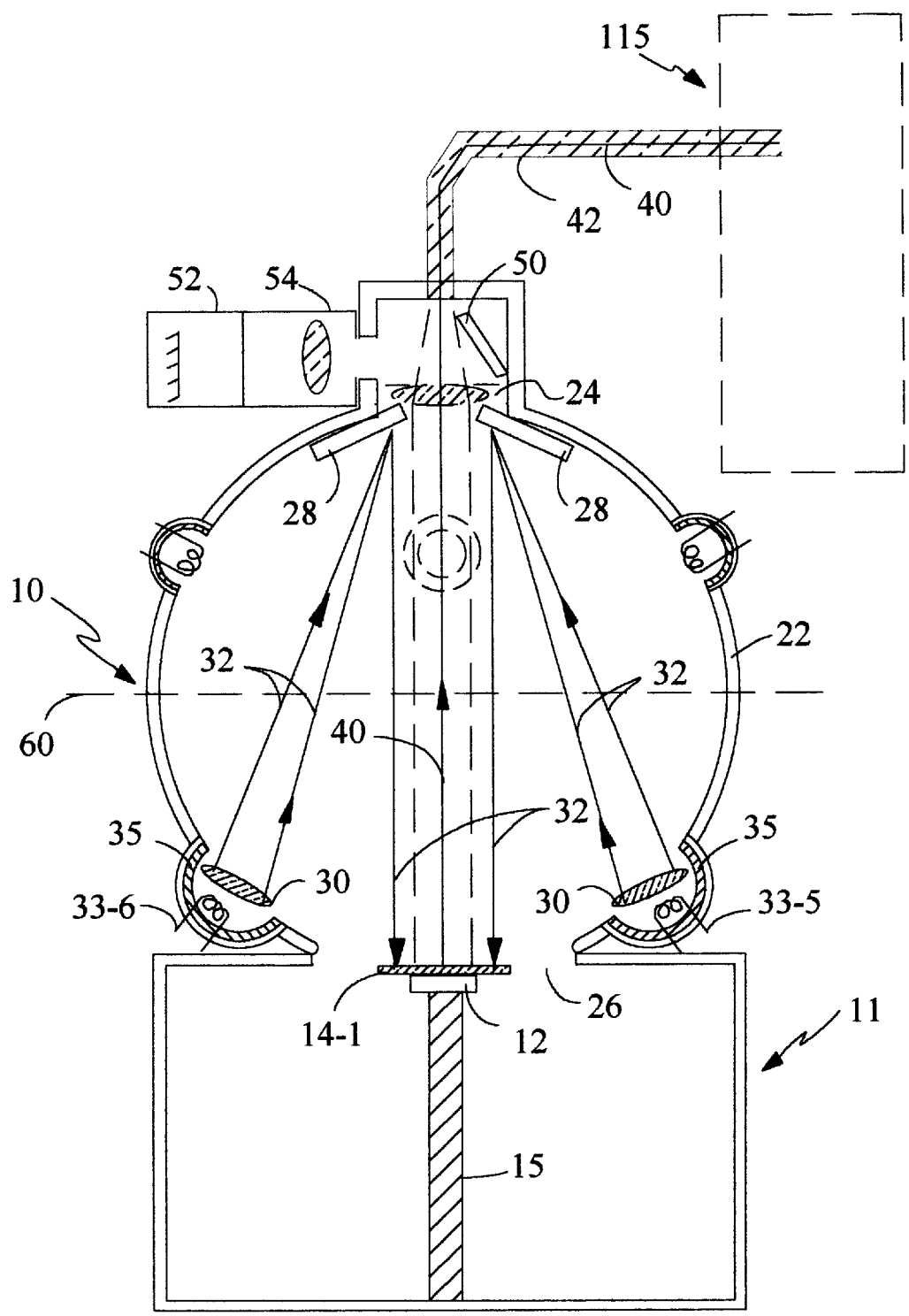
FIG. 3 is a sectional view of the optical system illustrated in FIG. 1 showing a variant of the lamp arrangement together with a diffuser for determining specular reflection.

Reflectometer 10, of FIG. 1, is the basic embodiment of the invention. However, the invention may include a modification which is useful to characterize a sample having a specular sample. A specular sample is one having a smooth or polished surface. Referring now to FIG. 3, a sectional view of the optical system illustrated in FIG. 1, is shown, together with the modification for determining the normal reflection to a specular sample. Spherical chamber 22 further includes a diffuse reflector 28. The reflector 28 is circumferentially disposed about the exit port 24 of the chamber 22. Here, lamps 33-5,6 are provided, with elliptical reflectors 35, below the horizontal axis 60, of the chamber 22. Projected light rays 32, from lamps 33-5,6, pass through converging lenses 30 in the direction of diffuser 28, such that rays 32 fall upon a specular sample 14-1, in a direction substantially normal to the surface of the cell. Reflected beam 40 is then emitted through exit port 24 for imaging 52, or dispersion, detection, determination and reporting 115, as described above.

Figure 4:
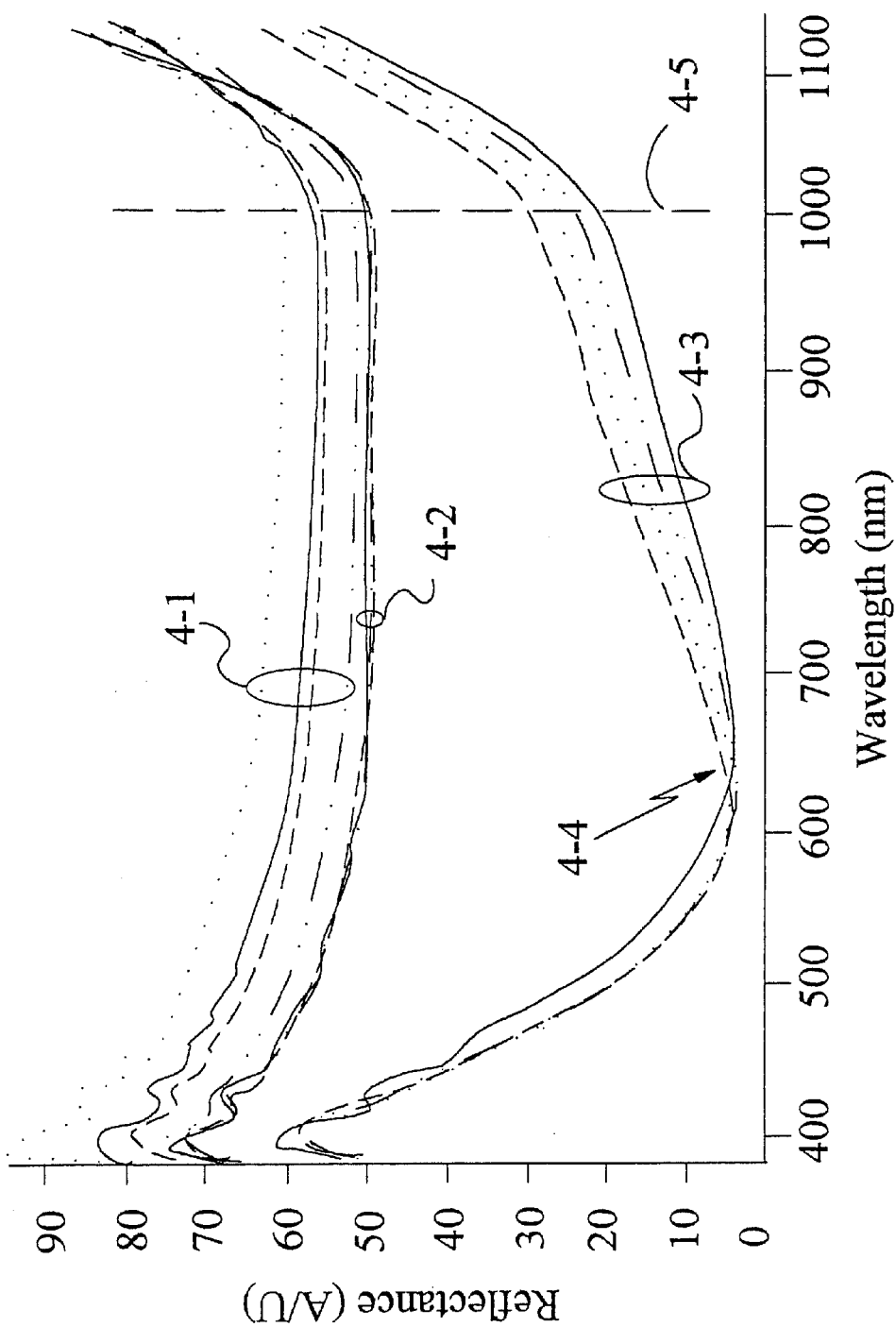
FIG. 4 is a reflection intensity distribution curve showing a comparison of the reflection intensity of four samples, during the sawed/cleaned, texture/etched, and film-coating fabrication steps.

Turning now to FIG. 4, a reflection intensity distribution curve is shown for comparison, of the optical quality, of four commercially sized, 4.5×4.5 inch, photovoltaic silicon wafers (shown as variations in line). The curve represents the determined reflection intensity of the normal reflection, plotted versus the wavelength, for each monochromatic component. The samples were monitored using the optical system of FIG. 1, Symmetric illumination was provided with lamps 33-1 and 33-2, of FIG. 1. These samples were monitored after the following three different stages in the fabrication process: (1) curves 4-1 illustrate the reflectance of the samples after texture-etching; (2) curves 4-2 illustrate reflectance of the samples after sawing and cleaning; and (3) curves 4-3 illustrate reflectance of the sample results after deposition of a $TiO_2$ antireflective-film coating.

As shown in FIG. 4, the sawing/cleaning fabrication step 4-2 demonstrates a high precision, sample to sample. In comparison, the texture/etching step 4-1 is less precise. Moreover, the antireflective-film coating step 4-3 has partially mitigated the variance attributable to the texture/etching step. The $TiO_2$ film thickness is 794–858 angstroms. This determination is made, as above, by finding the wavelength having the least reflectance 4-4 and then solving for the equation: $\lambda_o=4nt$. As shown in the Figure, the reflectance minimum 4-4, $\lambda_o$, is well-defined and, as a result of the strong signal for detection, is easily detected. The curves to the right of line 4–5 illustrate reflectance of the back-side contact. The graph was obtained over a 15 second interval. This interval included mounting and dismounting the sample, dispersion, detection, determination, and display of the results. The test measured reflectance over the full surface of the cell.

Figure 5A:
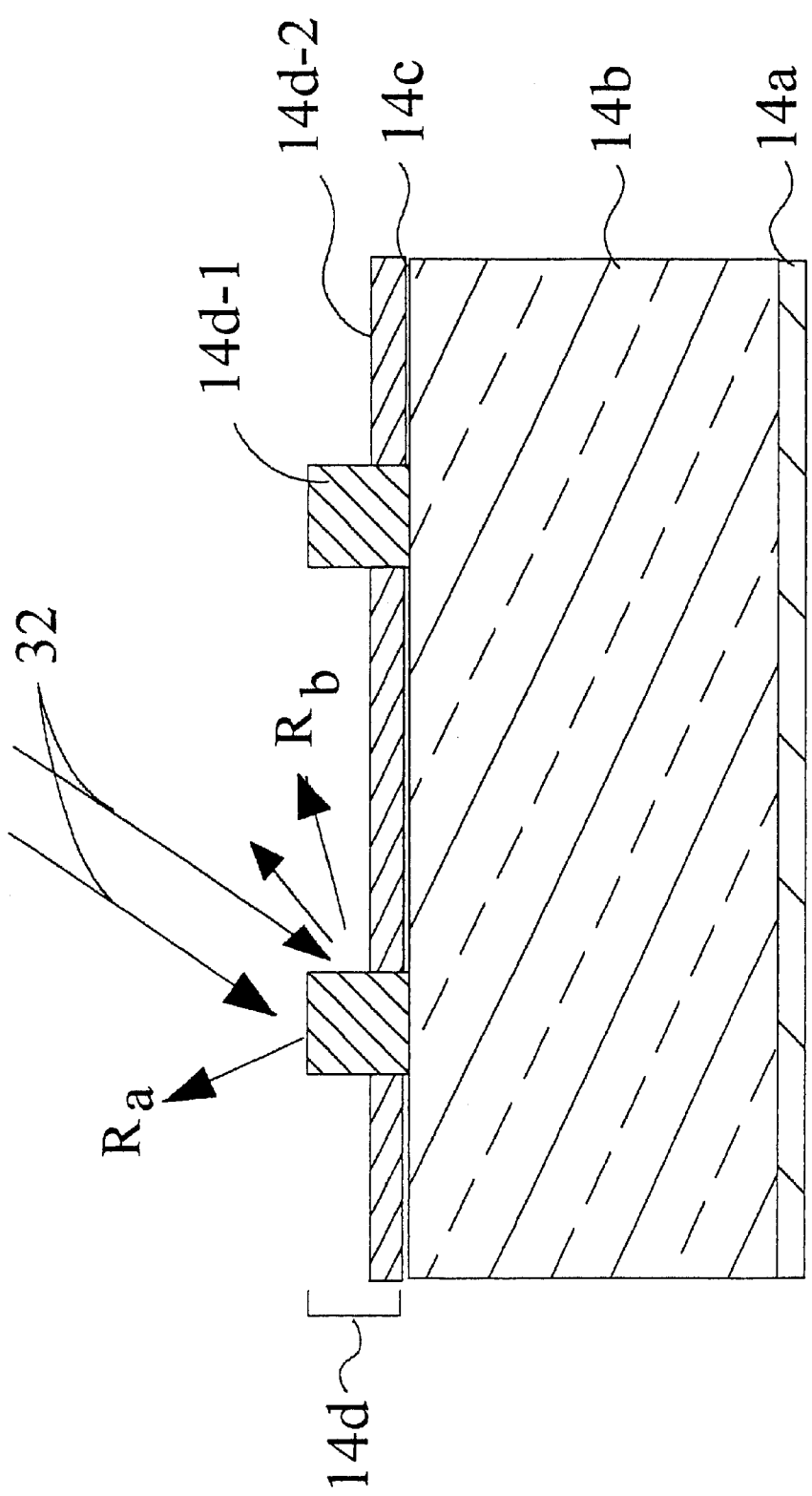
FIG. 5a is a sectional view of a silicon solar cell having an aluminum back-contact, and a front metal-contact.

With system 10, 115 of FIG. 1, calibrated and adjusted to a predetermined sensitivity, the invention is useful to determine the physical quality of the front or back metal-contacts of a sample cell 14. A cross section of a typical solar cell 14 is shown in FIG. 5a. In the Figure, the aluminum back-contact 14a supports a silicon layer 14b. Dielectric film 14c overlays silicon layer 14b. The front contact 14d is screen printed over the silicon layer 14b. The front contact includes a bus bar 14d-1 and finger 14d-2 configuration, in an asymmetric pattern. Thus, the optical characteristics of the front contact 14d change with the rotational orientation of the sample 14, on the sample support 12, of FIG. 1.

Figure 6:
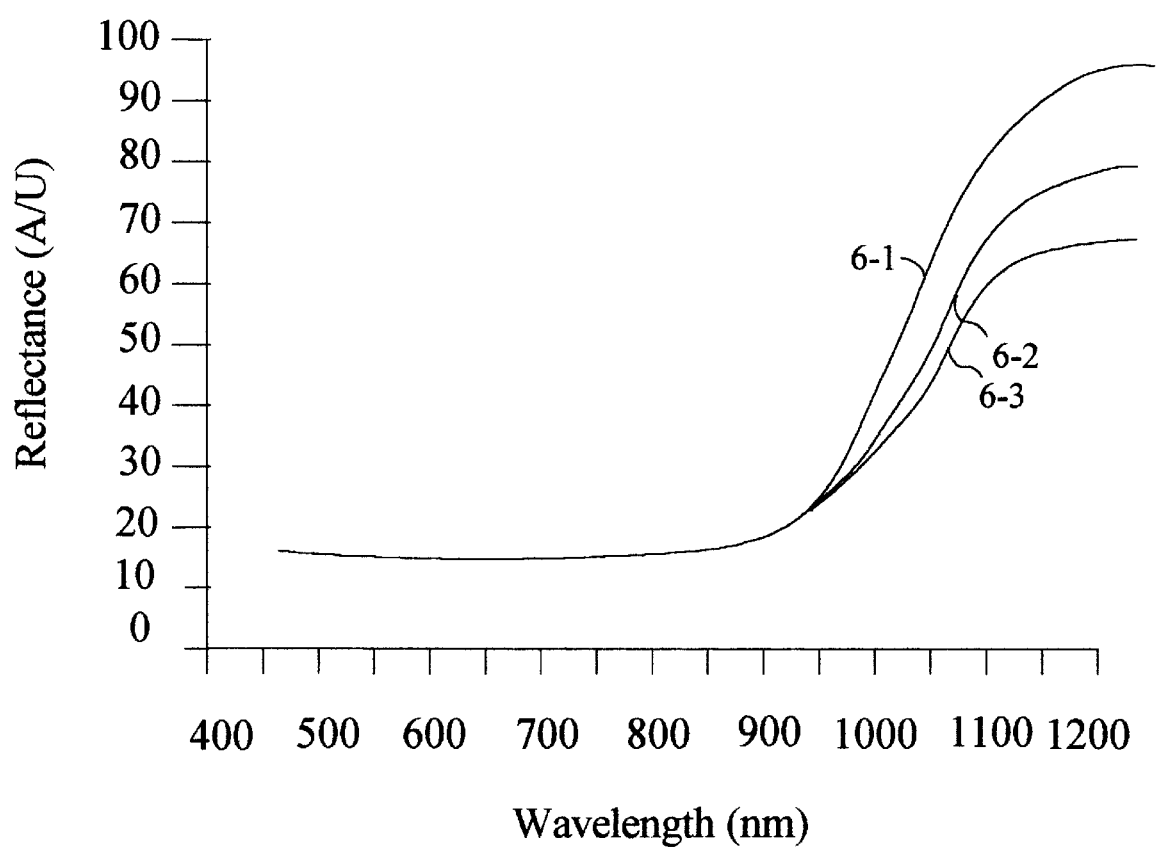
FIG. 6 is a reflection intensity distribution curve showing a comparison of the reflection intensity resulting from a high, and low, quality backside-contact.

A good quality silicon-aluminum back-contact exhibits a very high reflectance. Referring briefly to FIG. 1, a determination of the quality of the back-contact is made by illuminating sample 14 with lamps 33-1,2, and comparing the reported distribution curve obtained with that of a predetermined value, such as 90% reflectance. Reference is now made to FIG. 6, which is a reflectance intensity distribution curve, showing the difference in the back-side reflectance of three sample cells: A silicon control 6-2, a high-quality aluminum-contact 6-1, and a low-quality aluminum-contact 6-3. As the wavelength increases, there is greater penetration of the projected light into the silicon. As shown in FIG. 6, at about 1200 nm, more light is transmitted, which results in a reflectance from the backside-contact. The difference in reflectance between the high-quality contact 6-1, and the low-quality contact 6-3 is useful to monitor the precision of the contact fabrication process.

Referring once again to FIG. 5*a*, the configuration, and reflectance, of the front metal contact allows for a determination of the metal surface area, thickness, and symmetry. Symmetry is used to define the orientation of the printed metal pattern 14*d*, as the sample 14 is rotated 90 degrees on the sample support. Reflection intensity of the front contact 14*d*, is equal to the sum of the reflectance from bus bar 14*d*-1 and finger 14*d*-2 elements. In the Figure, Ra is the reflectance from the metal, upper, surfaces (area) of elements 14*d*-1 and 14*d*-2. Rb is the reflectance from light scattered by the step (thickness) surfaces of elements 14*d*-1 and 14*d*-2.

Figure 5B:
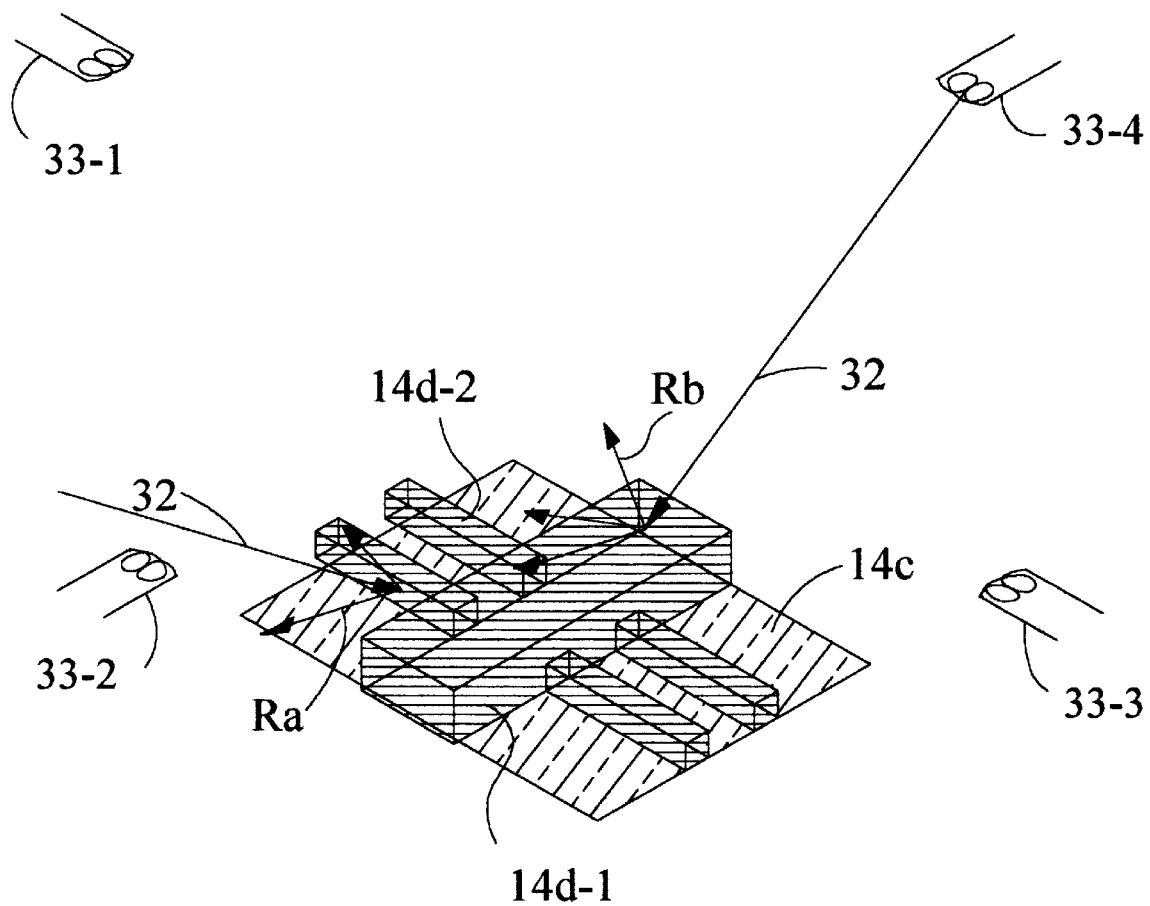
FIG. 5b is a three dimensional view of the solar cell illustrated in FIG. 5a showing the bus-bar and finger elements of the front metal-contact.

Referring now to FIG. 5*b*, it can be seen a three dimensional view of the solar cell illustrated in FIG. 5*a*. In the Figure, it is shown how the above configuration, taken in conjunction with directional illumination, can be used to determine the area, thickness, and symmetry of the front metal-contact 14*d*. When the sample surface 14*c*, 14*d*(1-2) is illuminated with lamps 33-(1–4), from all angles (symmetric illumination, not shown), a 90-degree rotation of the sample, on the support, will not cause a change in the total reflectance (Rt). However, as shown in the Figure, with directional illumination (asymmetric) parallel to the bus bar, from lamps 33-(2,4), applied, the reflectance Rb is primarily due to the upper surface of the bus bar (metal area). By changing the direction of the illumination (asymmetric illumination, not shown), from lamps 33-(2,4), to lamps 33(1,3) the reflectance Rb is now primarily due to the upper surface of the finger elements 14*d*-2.

Figure 7:
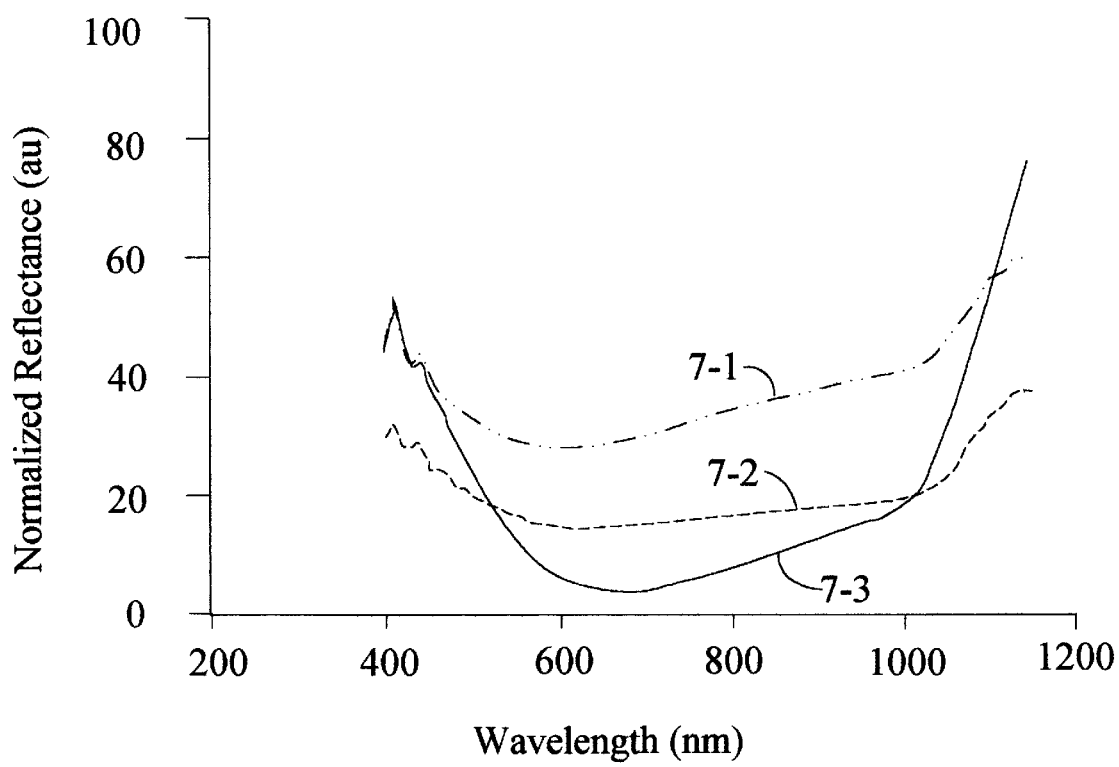
FIG. 7 is a reflection intensity distribution curve showing a comparison of three solar cells using asymmetric illumination to determine front-metallization.

Turning now to FIG. 7, it is shown, therein, a reflection intensity distribution curve for three solar cells in order to determine the symmetry of the front metal-contact. In the Figure, solid-line 7-3 is the reflectance (in arbitrary units) from a cell without front metallization; line 7-1 shows the reflectance from symmetric illumination, parallel to the bus-bar; and line 7-2 shows the reflectance from asymmetric illumination, perpendicular to the bus-bar. These differences in reflectance, from symmetric 7-1 to asymmetric 7-2, allow the computer to determine metallization of the front-contact, according to the following principles:

(1) Rt=(Rm+Rnm)
(2) (Rm)=(Ra+Rb)
(3) (Rnm)=Rsi or Rar/si where Rt is the total reflectance, Rm is the reflectance of the metal, Rnm is the reflectance of the non-metal, Ra and Rb is the reflectance related to the area and thickness of the metal (step), respectively, Rsi is the reflectance of the silicon, and Rar/si is the reflectance of the silicon and antireflective coating 14*c*, if any. Thus, where the cell has (1−x%) metal then x% is the area covered by the silicon Rsi, or coated 14-*c* silicon fraction Rar/si, of the cell. In most cases Rm is equal to Ra. Ra is a predictable constant, based on a predetermined result, and Rb varies with the direction of illumination.

The foregoing description is considered as illustrative only of the principles of the invention. For example, it is contemplated, that the optical system herein finds equal utility in the analysis of solar cells comprised of amorphous-silicon, cadmium-telluride, and copper-indium diselenide, and in the determination of a film thickness over these, and other, substrates. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

I claim:

1. An optical system for determining the physical characteristics of a solar cell, comprising:

(a) a lamp means for projecting light in a wide solid-angle onto the surface of the cell;

(b) a chamber for receiving the light through an entrance port, the chamber having an interior light absorbing spherical surface, an exit port for receiving a beam of light reflected substantially normal to the cell, a cell support, and a lower aperture disposed for releasing scattered light into a light absorbing baffle;

(c) a means for dispersing the reflection into monochromatic components;

(d) a means for detecting an intensity of the components; and (e) a means for reporting the intensity.

2. An optical system as defined in claim 1, wherein the reporting means comprises a computer having an input and an output, and a display, the input receptive to a signal corresponding to the intensity of the detected components, the computer determining a distribution curve of the intensity as a function of wavelength, and the output having a signal receptive to the display which is representative of the determination.

3. An optical system as defined in claim 2, wherein the determination includes comparing a surface texture, film, or metallization with a predetermined result.

4. An optical system as defined in claim 3, wherein determining the film includes finding a wavelength having a least intensity and calculating the film thickness.

5. An optical system as defined in claim 3, wherein the chamber further comprises a light diffusing means, the diffusing means deflecting the projection of light in a direction substantially normal to the cell surface, and the texture determination includes a specular surface.

6. An optical system as defined in claim 2, wherein the cell includes an upper metal layer having an asymmetric pattern, the lamp having a means for symmetric and asymmetric projection, and the determination includes finding an area, thickness, or a symmetry to the metal.

7. An optical system as defined in claim 2, wherein the display includes a monitor, printer, or plotter.

8. An optical system as defined in claim 1, wherein the light includes a 400–1,200 nm spectra.

9. An optical system as defined in claim 1, wherein the dispersion means includes a monochromater.

10. An optical system as defined in claim 1, wherein the support is a vacuum chuck smaller in size than the cell to be characterized.

11. An optical system as defined in claim 1, further comprising a fiber-optic cable for transmitting the reflection from the exit port to the dispersing means.

12. An optical system as defined in claim 1, further comprising a means for observing an image of the cell.

13. An optical system as defined in claim 12, wherein the means for observing includes a prism or mirror, for deflecting the reflection to an image plane.

14. An optical system as defined in claim 13, wherein the image plane includes a digital camera.

15. A method for monitoring the optical properties of a solar cell, comprising the steps of:
 (a) locating the cell in a light absorbing chamber, the chamber having an interior light absorbing spherical surface, and entrance port, an exit port, a cell support, and a lower aperture disposed for releasing scattered light into a light absorbing baffle;
 (b) projecting the light in a wide solid-angle, through the entrance port, at the cell surface;
 (c) reflecting a beam of light substantially normal to the cell surface;
 (d) dispersing the reflection into monochromatic components; and
 (e) detecting an intensity for the monochromatic components.

16. The method as defined in claim 15, including the step of determining a distribution curve of the normal reflection intensity as a function of wavelength.

17. The method as defined in claim 16, including the step of comparing a surface texture, dielectric film, or cell metallization with a predetermined result.

18. The method as defined in claim 16, wherein the step of projecting the light comprises alternating the illumination from symmetric to asymmetric, and further including determining an area, thickness, or symmetry of a front metal-contact to the cell.

19. The method as defined in claim 16, including the step of finding a wavelength having a least reflectance and determining thickness of the film.

20. The method as defined in claim 16, including the step of comparing the optical quality for a metal back-contact.

21. The method as defined in claim 16, including the step of providing an image of the cell.

22. The method as defined in claim 16, 17, 19, 20, or 21 including the step of displaying the comparison, determination, or image on a monitor, printer, or plotter.

* * * * *